US012161362B2

(12) United States Patent
Corr et al.

(10) Patent No.: US 12,161,362 B2
(45) Date of Patent: Dec. 10, 2024

(54) IMAGE-GUIDED TISSUE ACCESS DEVICE

(71) Applicant: Baylor College of Medicine, Houston, TX (US)

(72) Inventors: Stuart James Corr, Houston, TX (US); Andrew Anderson, Pearland, TX (US); Eric Lewis, Houston, TX (US); Brian Dawson, Houston, TX (US); Rocky Chang Browder, Houston, TX (US); James Suliburk, Houston, TX (US)

(73) Assignee: Baylor College of Medicine, Houston, TX (US)

(*) Notice: Subject to any disclaimer, the term of this patent is extended or adjusted under 35 U.S.C. 154(b) by 101 days.

(21) Appl. No.: 17/756,632

(22) PCT Filed: Nov. 19, 2020

(86) PCT No.: PCT/US2020/061319
§ 371 (c)(1),
(2) Date: May 27, 2022

(87) PCT Pub. No.: WO2021/113085
PCT Pub. Date: Jun. 10, 2021

(65) Prior Publication Data
US 2022/0409233 A1     Dec. 29, 2022

Related U.S. Application Data

(60) Provisional application No. 62/943,566, filed on Dec. 4, 2019.

(51) Int. Cl.
*A61B 8/00*     (2006.01)
*A61B 8/08*     (2006.01)
(Continued)

(52) U.S. Cl.
CPC .......... *A61B 17/3403* (2013.01); *A61B 8/085* (2013.01); *A61B 8/4209* (2013.01);
(Continued)

(58) Field of Classification Search
CPC ... A61B 17/3403; A61B 8/085; A61B 8/4209; A61B 8/0841; A61B 2017/00876;
(Continued)

(56) References Cited

U.S. PATENT DOCUMENTS 5,758,650 A    6/1998  Miller et al.
6,485,426 B2  11/2002  Sandhu
(Continued)

OTHER PUBLICATIONS

International Search Report dated Feb. 17, 2021 entered during examination of International Application No. PCT/US2020/061319.

*Primary Examiner* — Patrick Fernandes
*Assistant Examiner* — Zainab Mohammed Aldarraji
(74) *Attorney, Agent, or Firm* — Norton Rose Fulbright US LLP

(57) ABSTRACT

Embodiments of the disclosure include a tissue and/or access device that allows for adjustability of placement of a needle for accessing a blood vessel of an individual in need thereof, particularly when used with an imaging device. The adjustability originates from both angle of the needle for insertion into the body of the individual and longitudinal placement of the needle on the body of the individual. In specific embodiments, a needle guide through which the needle traverses is detachable.

21 Claims, 11 Drawing Sheets

(51) Int. Cl.
*A61B 17/00* (2006.01)
*A61B 17/34* (2006.01)

(52) U.S. Cl.
CPC ............... *A61B 2017/00876* (2013.01); *A61B 2017/3407* (2013.01); *A61B 2017/3411* (2013.01); *A61B 2017/3413* (2013.01)

(58) Field of Classification Search
CPC .... A61B 2017/3407; A61B 2017/3411; A61B 2017/3413
See application file for complete search history.

(56) References Cited

U.S. PATENT DOCUMENTS

| | | | |
|---|---|---|---|
| 6,814,704 B2 | 11/2004 | Weilandt | |
| 2002/0133079 A1* | 9/2002 | Sandhu | A61B 8/4209 600/464 |
| 2005/0267373 A1 | 12/2005 | Lee | |
| 2014/0276081 A1* | 9/2014 | Tegels | A61B 8/4209 600/461 |
| 2016/0128719 A1* | 5/2016 | Cermak | A61B 17/3403 600/461 |
| 2019/0059854 A1* | 2/2019 | Radl | A61B 8/4455 |
| 2019/0282262 A1* | 9/2019 | Bouazza-Marouf | A61B 17/3403 |

\* cited by examiner

FIG 4.0

IMAGE-GUIDED TISSUE ACCESS DEVICE

This application is a national phase application under 35 U.S.C. § 371 that claims priority to International Application No. PCT/US2020/061319 filed Nov. 19, 2020, which claims priority to U.S. Provisional Patent Application Ser. No. 62/943,566, filed Dec. 4, 2019, both of which are incorporated by reference herein in their entirety.

TECHNICAL FIELD

Embodiments of the technical field of the disclosure concern at least medical devices, including medical procedure tools.

BACKGROUND

Catheter-based interventions account for 29% of all central and peripheral procedures. As this market is anticipated to increase in the future, the need for safe vascular access has never been greater [1]. Currently groin hematomas are the most common complications with reported rates between 3-4.5% after peripheral interventions [2]. Risk factors include age greater than 80, obesity and sheath sizes greater than 6 Fr. Patients with symptomatic groin hematomas (pain, infection, overlying skin necrosis) must undergo surgical evacuation and repair [3]. Other complications include retroperitoneal hematoma, groin pseudoaneurysm and iatrogenic arteriovenous fistula.

Retroperitoneal hematomas occur secondary to high arterial puncture during access above the inferior epigastric artery. Although rarer than groin hematomas, potential complications of retroperitoneal hematomas can be fatal. Treatment is based on an individual basis but can include endovascular intervention with a covered stent or open surgical decompression and repair [4].

Groin pseudoaneurysms occur at a rate of less than 1% in contemporary literature [5-6] but differ from groin hematomas due to the presence of active arterial flow from the prior arteriotomy site. The most common etiology of groin pseudoaneurysm relate to inadequate pressure or failure of closure devices post procedures. This is often due to superficial femoral arterty (SFA) or low common femoral artery (CFA) access as the soft tissue in this area is insufficient for adequate compression. Treatment occurs when the pseudoaneurysm is symptomatic (pain, persistent anemia) or increases in size after a period of observation [7-9].

Iatrogenic arteriovenous fistulas are another rare complication with incidences reported between 0.5 and 0.86% after intervention [10-12]. This occurs when a connection is created between the femoral vein and artery and is a direct complication of trauma secondary to incomplete visualization of the needle tip [11]. Arterial venous fistulas (AVF) may occur with low through and through punctures of the CFA and inadvertent puncture of the profunda artery and vein [11]. While 38% of all groin AVF close spontaneously within 12 months, symptomatic or enlarging AVF will require either endovascular or surgical treatment [13-15].

Femoral access is optimally attained at the common femoral vessels which lie in the "femoral triangle" [16]. It is an anatomical region which is contained by the inguinal ligament superiorly, the sartorius muscle laterally and the adductor longus medially. Significant structures contained within this space include the femoral artery and vein as well as the femoral nerve [17].

Classically, femoral access is obtained by identifying the anatomic landmarks of the anterior superior iliac spine and pubis. This line created between the two landmarks marks the theoretical inguinal ligament and arterial access obtained by dividing this line in half and palpating for the femoral pulse medially and distally. Venous access can also be obtained just medial to the arterial pulsation. Since the advent of ultrasound however, access via anatomic landmark has become less common as direct visualization has become the standard of care [16].

BRIEF SUMMARY

Embodiments of the disclosure concern systems, devices and methods of overcoming complications associated with access to tissues and/or organs in an individual. In specific embodiments, the devices and methods overcome complications associated with access to a vessel in an individual. In particular embodiments, the disclosure provides systems and methods for using an adjustable needle positioning device having a detachable needle guide. The device of the disclosure includes any imaging (including by ultrasound) tissue and/or organ access device designed to provide safe, rapid and facile tissue and/or organ (including vascular) access for an individual. In specific embodiments, it is a fully adjustable and detachable system that is used in conjunction with imaging devices of any kind to provide image-guided tissue and/or organ (such as vascular) access. It can be applied to a wide range of applications, such as catheter-based procedures, tumor biopsies, drug delivery, and general surgical procedures involving percutaneous access.

In particular embodiments, the system of the disclosure allows for adjustments to be made for positioning of a needle in at least two manners. In one manner, a location of a needle with respect to any surface of a body is adjusted along the plane of the surface of the body to provide for refinement of positioning of the needle. In another manner, the angle upon which the needle is positioned on approach for insertion of the needle percutaneously into the body is adjusted to provide a smaller angle or larger angle with respect to the plane of the surface of a body.

The system, methods, and compositions of the disclosure may be applied to a wide range of applications, such as tumor biopsies, drug delivery, and general surgical procedures involving percutaneous access.

Embodiments of the disclosure encompass a system for facilitating access to tissue and/or organ using an imaging device, comprising: (a) a body component having four sides, wherein said body component is configured to have the imaging device insertable therein, wherein the body optionally has an opening suitably sized to transmit an image; (b) a needle guide comprising a longitudinal axis along its length and comprising a width, wherein the needle guide is rotationally moveable along the longitudinal axis and wherein there is at least one opening that traverses the width of the needle guide, wherein the opening is suitably sized for positioning a needle; (c) a needle guide positioning apparatus comprising one or more arms and comprising means for inserting the needle guide therein, wherein at least two of the sides of the body comprise tracks through which the arms of the needle guide positioning apparatus are insertable therein, and wherein the needle guide is detachable from the needle guide positioning apparatus. In specific embodiments, the system is further defined as a system for facilitating access to a vessel. The body may or may not comprise one or more mounting components configured to hold the ultrasound device in the body. In specific cases, the needle guide comprises 1, 2, 3, 4, 5, 6, or more openings that traverse the width of the needle guide. Multiple of the openings may comprise different sizes to accept needles of different gauges, for example.

In particular embodiments for the body of the device, the tracks on the body comprise one or more holes, one or more notches, one or more nodules, one or more magnets, or a combination thereof. In some cases, the arms of the needle guide positioning apparatus each comprise an interior side and an exterior side, wherein when the needle guide positioning apparatus is not in the tracks of the body, the interior sides of the arms face one another. The interior sides of the arms may comprise one or more holes, one or more notches, one or more nodules, one or more magnets, or a combination thereof. In specific cases, the tracks on the body and the interior sides of the arms of the needle guide positioning apparatus comprise corresponding one or more holes, one or more notches, one or more nodules, one or more magnets, or a combination thereof. In particular embodiments, the body is configured as a parallelogram and a first parallel pair of two sides is the same or longer length as a second parallel pair of two sides. One or both of the first parallel pair of two sides and second parallel pair of two sides may have tracks through which the arms of the needle guide positioning apparatus are insertable therein.

In particular embodiments, the needle guide positioning apparatus comprises a means for inserting the needle guide therein that is magnetic, ferromagnetic, superparamagnetic, electro-magnetic, is a manufactured channel, or a combination thereof. In at least some cases, the needle guide positioning apparatus comprises a handle. The needle guide may comprise two or more components that are configured to be interlockable and/or detachable from one another. In specific cases, the imaging device is an ultrasound device.

In one embodiment, there is a method of accessing a region of a tissue and/or organ of an individual by needle and with an imaging device, comprising the step of moveably positioning the needle at the body of the individual using any system of the present disclosure. In some cases, the method may be further defined as using a signal from the imaging device to provide information about the tissue and/or organ of the individual, wherein the information informs a user of the system about a desired location and/or angle for the needle. The method may be further defined as positioning the system at the body of the individual and slideably moving the needle guide positioning apparatus to allow for a desired position of the needle at the body. The method may be further defined as rotating the needle guide along the longitudinal axis to position the needle at a desired angle with respect to the body of the individual.

In specific embodiments, following positioning of the needle at the body, the needle guide is detached from the system. In some cases, following positioning of the needle at the body, the needle guide is detached from the system and the needle guide is detached from the needle. The method may be further defined as wherein two separate of the devices are respectively configured for and are respectively used for transverse and longitudinal imaging-guided needle access. In some cases, there is only image-guided tissue access device utilized, and the one device is configured for transverse and/or longitudinal imaging-guided needle access, said device incorporating both longitudinal and transverse rail guides and relative components thereof.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value. The term "about" may refer to angles of needle access percutaneously to a body surface, in which case the needle may be adjusted "about" X degrees or within 1, 2, 3, 4, 5, 6, 7, 8, 9, or 10 degrees of X degrees, as one example. The term "about" may also refer to the distance along the surface of a body along which a rail guide may be adjusted, in which case the rail guide may be moved "about" X millimeters (mm) or within 1, 2, 3, 4, 5, 6, 7, 8, 9, or 10 mm, as one example.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the disclosure may apply to any other embodiment of the invention. Furthermore, any composition of the disclosure may be used in any method of the invention, and any method of the disclosure may be used to produce or to utilize any composition of the invention. Aspects of an embodiment set forth herein are also embodiments that may be implemented in the context of embodiments discussed elsewhere in the application, such as in the Brief Summary, Detailed Description, Claims, and Brief Description of the Drawings.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure. Additional objects, features, aspects and advantages of the present invention will be set forth in part in the description which follows, and in part will be obvious from the description or may be learned by practice of the invention. Various embodiments of the disclosure will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present disclosure is best defined by the appended claims.

DETAILED DESCRIPTION

Figure 1:
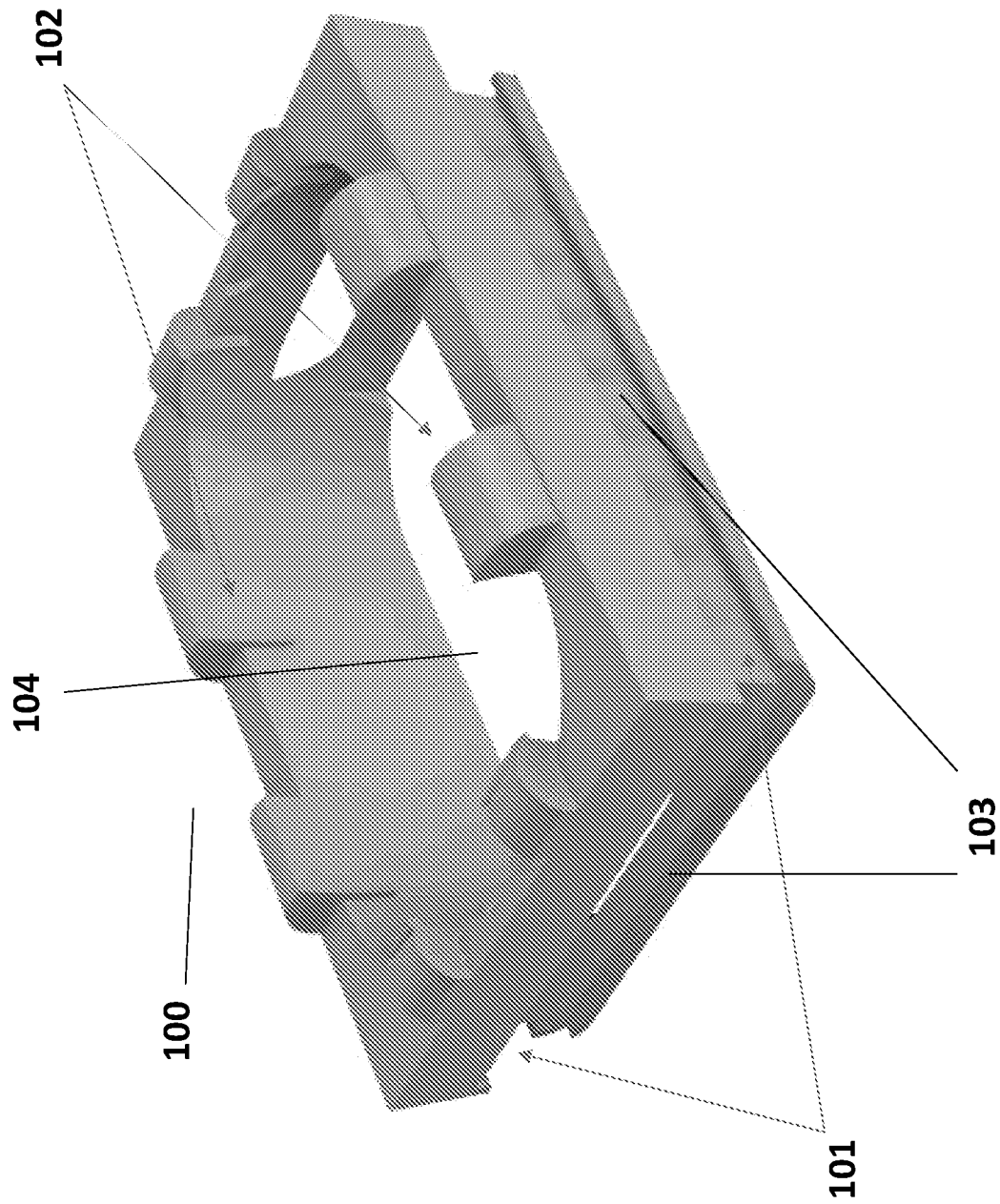
FIG. 1 shows one example of a body of a vascular access device for use with an ultrasound device.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

I. Tissue Access Device

The device of the disclosure is a fully adjustable and removable needle positioning device that allows for rapid, simple and accurate access to any tissue and/or organ in the body (or outside if the body, for example in tissue engineering and/or transplant) of an individual for any purpose. In specific embodiments, the device is used to insert a medical tool (e.g., catheter or wire) into the body, and in other cases the device is used to remove an entity from the body, such as tissue, including for analysis of any kind (for example, a biopsy). The tissue being accessed may or may not be vascular. The tissue may be of the brain, heart, lungs, muscle, fat, liver, kidney, pancreas, appendix, spleen, gall bladder, uterus, testis, stomach, colon, bone, and so forth.

In particular embodiments, the needle positioning device allows for rapid, simple and accurate vascular (intravenous or intraarterial) access. Once gained, vascular access can allow for a variety of procedures to take place, such as guidewire and catheter insertion, cannulation, needle biopsies, etc. This device allows for either specialized or non-specialized medical staff to gain vascular access at a variety of entry points, including subclavian, jugular, femoral, etc. The device is applicable to a broad range of procedures where precise and accurate insertion of a needle or similar is needed at a variety of entry points, such as percutaneous tumor/tissue biopsy, vascular access via femoral, jugular, subclavian access points, etc. As used herein, the term "access" refers to the ability of at least the tip of a needle to enter into the lumen of a blood vessel, as well as entry into tissues, organs, tumor, bones, intraperitoneal space, cavities or any other biological compartment in a mammal, including a human, dog, cat, horse, cow, and so forth. The device can also be used for medical educational training purposes using non-biological patients/samples, such as phantoms and simulations.

In particular embodiments, the device is a fully adjustable and removable needle positioning device with a detachable needle guide. The device is configured and used in conjunction with an imaging device, such as an ultrasound transducer, to allow for precise needle visualization and positioning. The detachable needle guide allows for the main body of the device to be removed without disturbing the inserted needle. The device, in one embodiment, comprises a main body that attaches to an ultrasound transducer. The body of the device holds rails to move the needle positioning guide either closer to or further away from the main body of the device. Once vascular access has been obtained, the needle guide can be completely removed from the device. Any component of the device may either be fully disposable or reusable.

In particular embodiments, the vascular access device of the disclosure comprises at least three parts: (1) body; (2) rail guide (which may also be referred to as a needle guide positioning apparatus); and (3) needle guide. FIGS. 1-11 illustrate components of the device and certain configurations of their combinations.

A. Body

FIG. 1 illustrates one embodiment of the body of the device. In particular embodiments, the body 100 is configured to receive a transducer section of any imaging device, such as a hand-held ultrasound imaging device 800, such as the Butterfly IQ system. The body 100 has four sides and may be configured as a parallelogram that may be a rectangle or a square, for example. The body 100 may be selected based on the shape of the corresponding transducer section of the imaging device. The body 100 has an opening 104 suitable in shape and size to allow an ultrasound device, for example, to transmit and receive ultrasound energy for data acquisition and image reconstruction. In some cases, the body 100 lacks the opening 104 and is solid, so long as the material is suitable for transmitting and receiving ultrasound energy for data acquisition and image reconstruction. This body component 100 comprises rail guide insertion points 101 whereby in FIG. 2 the rail guide arms 201 are configured to slide in and out of the insertion points 101 to allow for easy length adjustment.

Rail guide tracks 103 comprise tracks along the side of the body 100 that are sized and configured to accept rail guide arms 201. A pair of rail guide tracks 103 on opposite sides of the body 100 are generally parallel to one another. In some embodiments, body 100 comprises a first pair of rail guide tracks 103 that are generally parallel to one another and also comprises a second pair of rail guide tracks 103 that are generally parallel to one another but are positioned on the body 100 90 degrees with respect to the first pair. In other embodiments the body 100 comprises only one pair of rail guide tracks 103 that are generally parallel to one another. The body 100 may be configured to allow the rail guide arms 201 to be orientated in either the longitudinal or transverse axis (FIG. 4.0) of the imaging plane (see also FIGS. 9 and 10 that illustrate the configuration for longitudinal and transverse imaging planes, respectively).

Rail guide insertion points 101 and corresponding rail guide tracks 103 can comprise a variety of different locking patterns and/or mechanisms to allow for easy adjustability of the rail guide yet provide adequate gripping strength. For example, rail guide insertion points 101 and corresponding rail guide tracks 103 can comprise such physical characteristics as alligator teeth, cross-hatching, triangular patterning, square patterning, circular patterning, fragmented patterning, or a combination thereof, that facilitate sufficient holding of the rail guide arms 201 within the rail guide tracks 103. In additional or alternative embodiments, the rail guide insertion points 101 and corresponding rail guide tracks 103 are magnetic and/or utilize friction, elasticity, polymer coatings, or a combination thereof to provide such a controlled adjustable mechanism for the rail guide 200 to be inserted into the rail guide insertion points 101 and allow gripping yet mobility of the rail guide arms 201 within the rail guide tracks 103.

Figure 5:
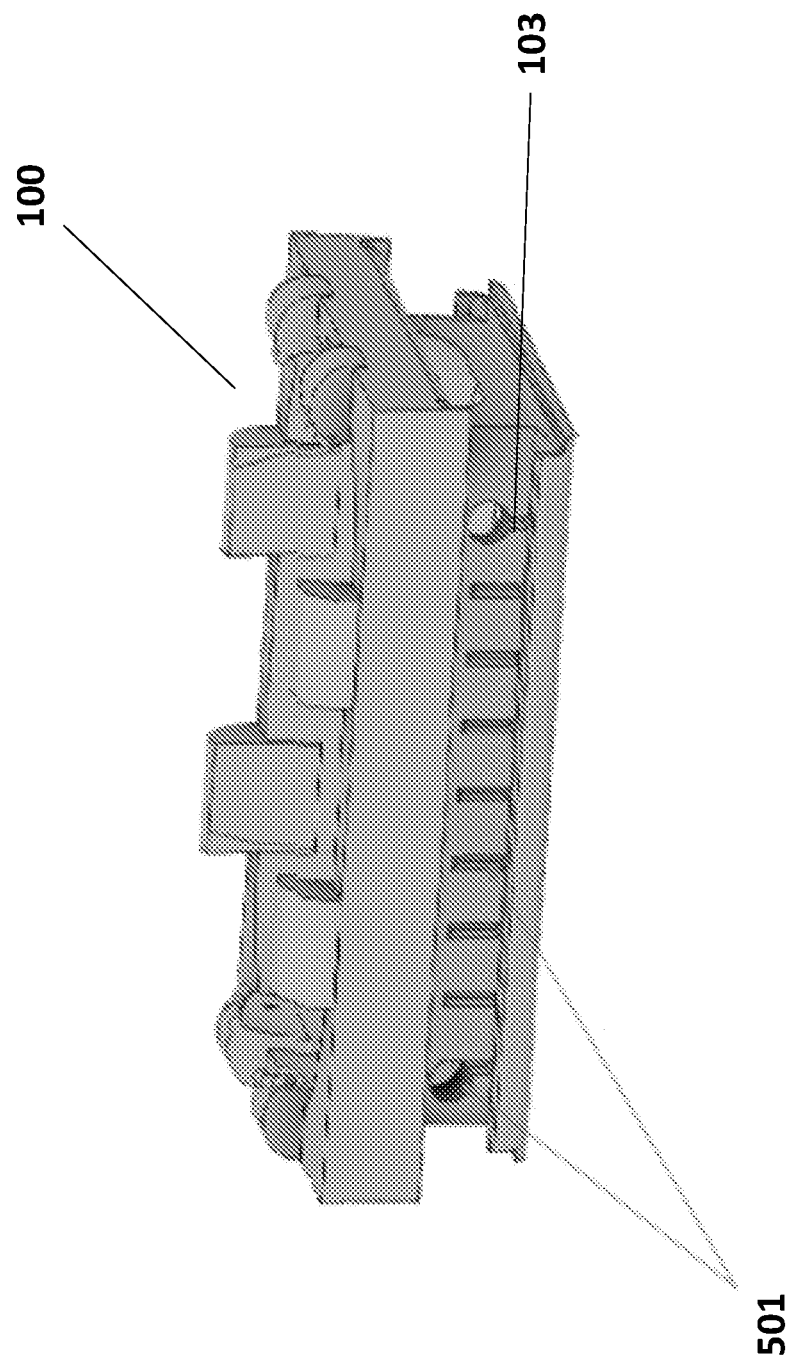
FIG. 5 illustrates one example of a body of a vascular access device having pre-indented holes or notches along tracks on the body for arms of a rail guide to be inserted. Examples of notches in the tracks to facilitate grip of the rail guide into the tracks on the body are shown.

In some embodiments, the rail guide insertion points 101 and rail guide tracks 103 can be comprised of either pre-indented holes and/or notches 501 and/or nodules and/or magnets (FIG. 5 shows one example of both a magnetic and a groove mechanism).

FIG. 1 also shows the body comprising an example of multiple transducer mounting components 102. The body 100 may have 1, 2, 3, 4, 5, or more transducer mounting components 102 along 1, 2, 3, or all sides of the body. In specific cases there are two transducer mounting components 102 on each side of the body 100. The shape of the transducer mounting components 102 may be of any kind so long as they are able to secure an imaging device in the body 100. All of the transducer mounting components 102 may or may not be of the same shape. In specific cases, the transducer mounting components 102 are generally curved toward the interior of the body 100. Transducer mounting components 102 may be pre-configured with a variety of different transducer heads such that the transducer mounting components 102 allow for multiple different devices to be used. In specific cases, the transducer mounting components 102 are configured to be a clip-on mechanism that secures the transducer section of the imaging device. The transducer mounting components 102 may be adjustable clips, and in some cases, a separate adapter and/or device and/or mounting object may be fitted into the body 100 to allow for other transducer heads to be used with the device. The term "adapter" as used herein refers to an entity that can be inserted into opening 104 that would allow another type of transduced head to be utilized.

B. Rail Guide

Figure 2:
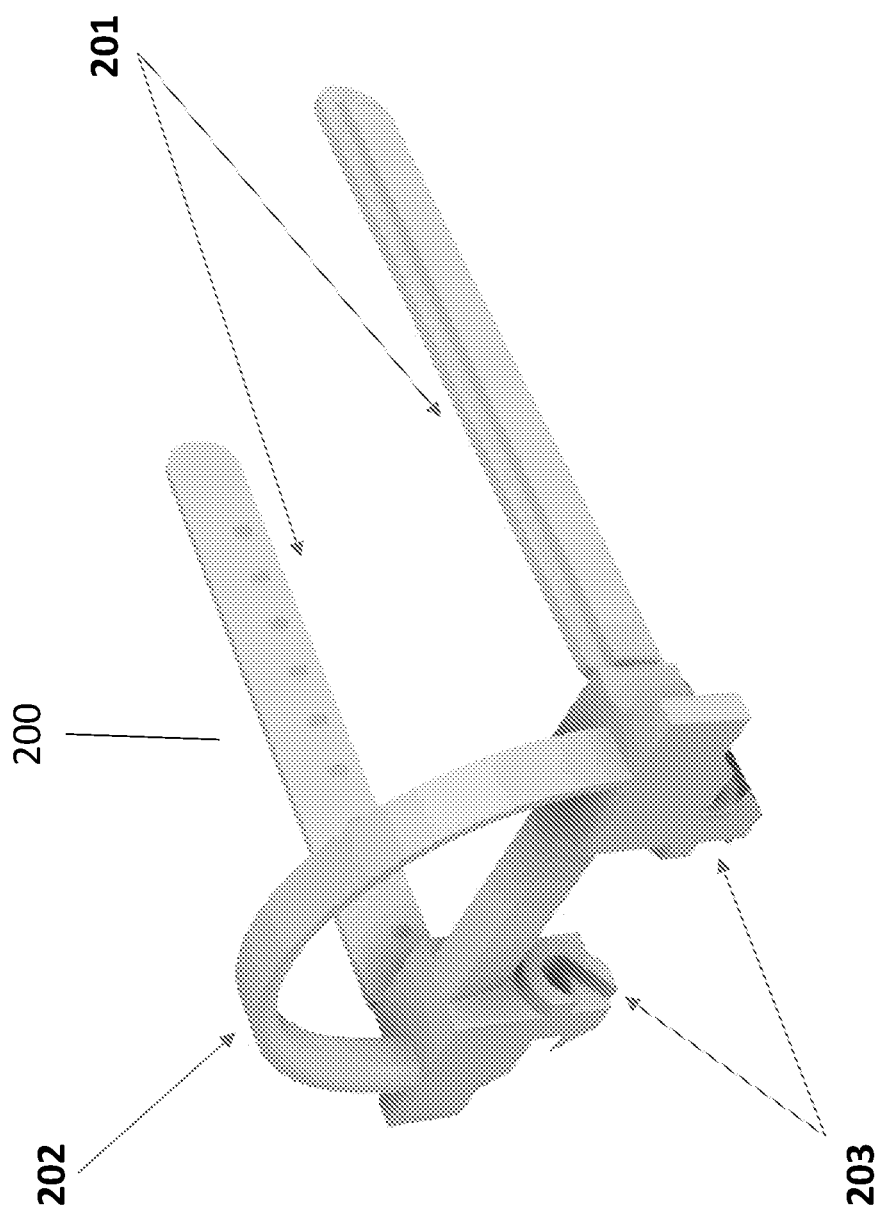
FIG. 2 illustrates one example of a rail guide to be employed in a body of a vascular access device.

FIG. 2 illustrates one embodiment of the rail guide 200 of the device. In specific embodiments, the rail guide 200 serves two functions. First, the rail guide 200 allows adjustment and positioning of the needle guide 300 (FIG. 3) along a single axis via insertion into the rail guide insertion points 101 controlled via the adjustment point 202. Second, the rail guide 200 allows for both holding and quick release of the needle guide 300.

The rail guide 200 can be comprised of a variety of materials with a variety of different properties depending on desired use. The rail guide 200 is designed to be completely detachable from the body 100. The rail guide 200 is designed to allow for smooth and facile length adjustments along one axis without introducing jerking or hindering artifacts into the work-flow and imaging sequence.

The rail guide 200 comprises two rail guide arms 201 that are generally parallel to one another and connected at one end each of the rail guide arms 201 by an adjustment point 202. The adjustment point 202 may be of any shape so long as it allows concerted movement of the rail guide arms 201. In specific embodiments, the adjustment point 202 comprises a handle for gripping by a hand and that allows movement of the rail guide arms 201 within the rail guide tracks 103 at generally the same time. The interior sides of the rail guide arms 201 may be configured to have physical characteristics that allow for improved gripping of the rail guide arms 201 within the rail guide tracks 103. In such cases, the physical characteristics of the interior side of the rail guide arms 201 may correspond to generally the same physical characteristics of the rail guide tracks 103. As examples, the interior side of the rail guide arms 201 and the rail guide tracks 103 each may comprise alligator teeth patterning, cross-hatch patterning, triangular patterning, square patterning, circular patterning, fragmented patterning, or a combination thereof. In specific embodiments, the interior side of the rail guide arms 201 and the rail guide tracks 103 each may be magnetic, ferromagnetic, superparamagnetic, comprise friction, be elastic, comprise polymer coatings, or a combination thereof. These examples of physical attributes may be used to provide such a controlled adjustable rail guide mechanism that inserts into the rail guide insertion points 101 on the body 100.

Figure 6:
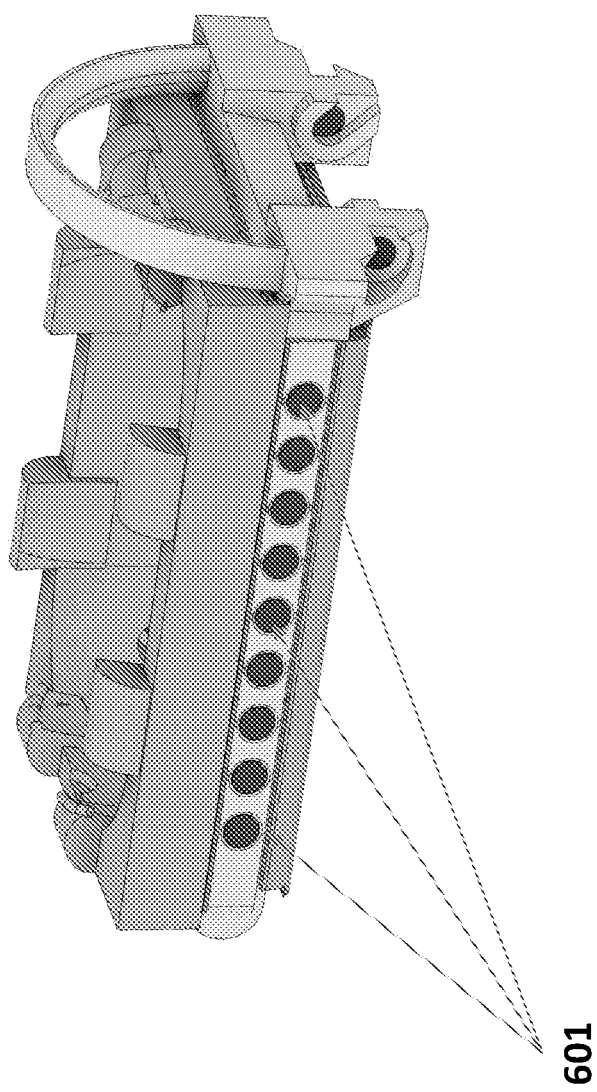
FIG. 6 demonstrates an embodiment of a rail guide having rail guide arms inserted into rail guide tracks of the body of a vascular access device. Examples are provided in which an array of magnets on the rail guide arms align with complimentary magnets within the rail guide tracks of the body.
Figure 7:
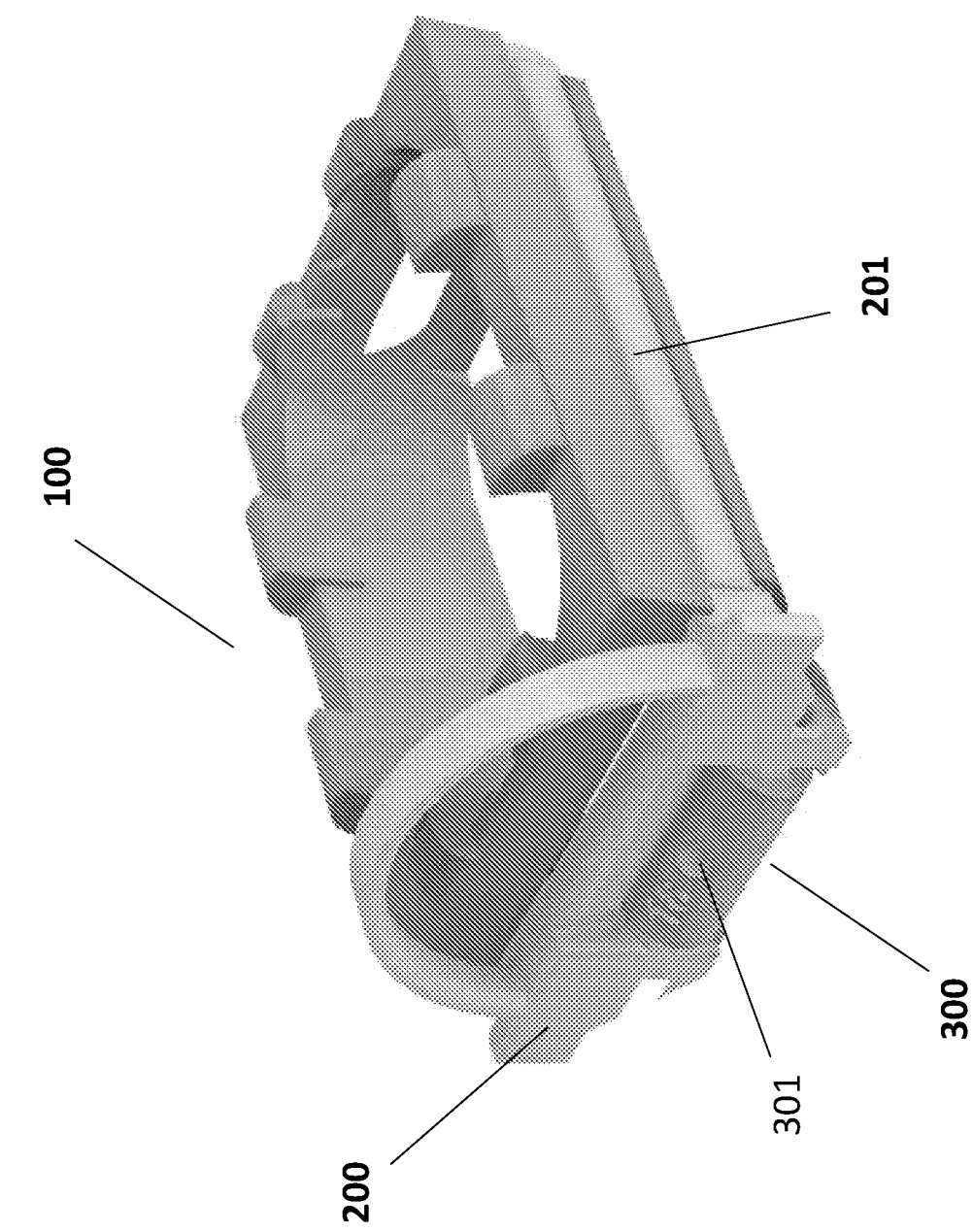
FIG. 7 shows one embodiment of a system having a movable rail guide slidably within a body of a vascular access device and a needle guide inserted into one end of the rail guide.
Figure 8:
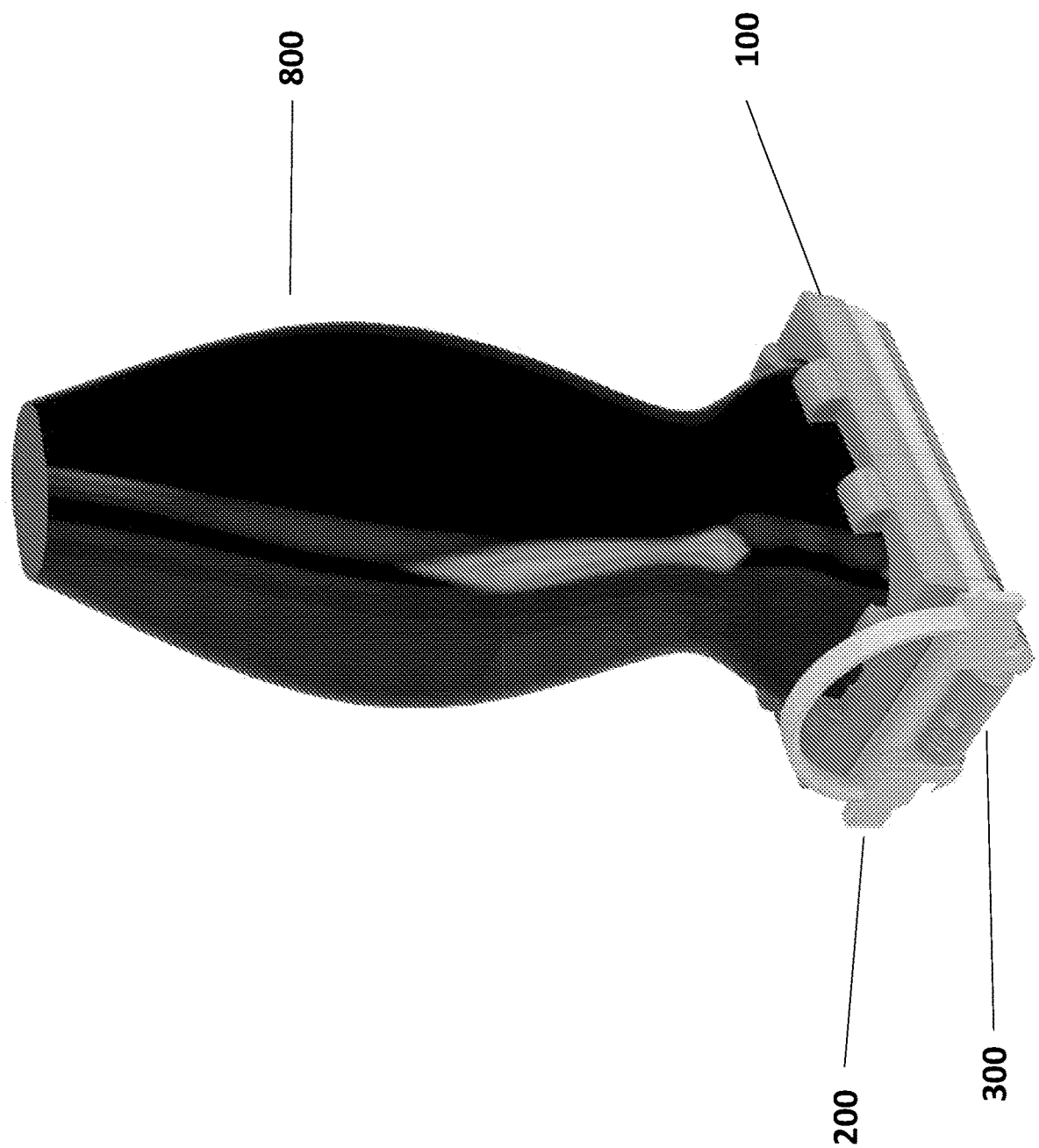
FIG. 8 shows one example of an ultrasound imaging device inserted into the body of a vascular access device configured for imaging in the longitudinal ultrasound imaging plane.
Figure 9:
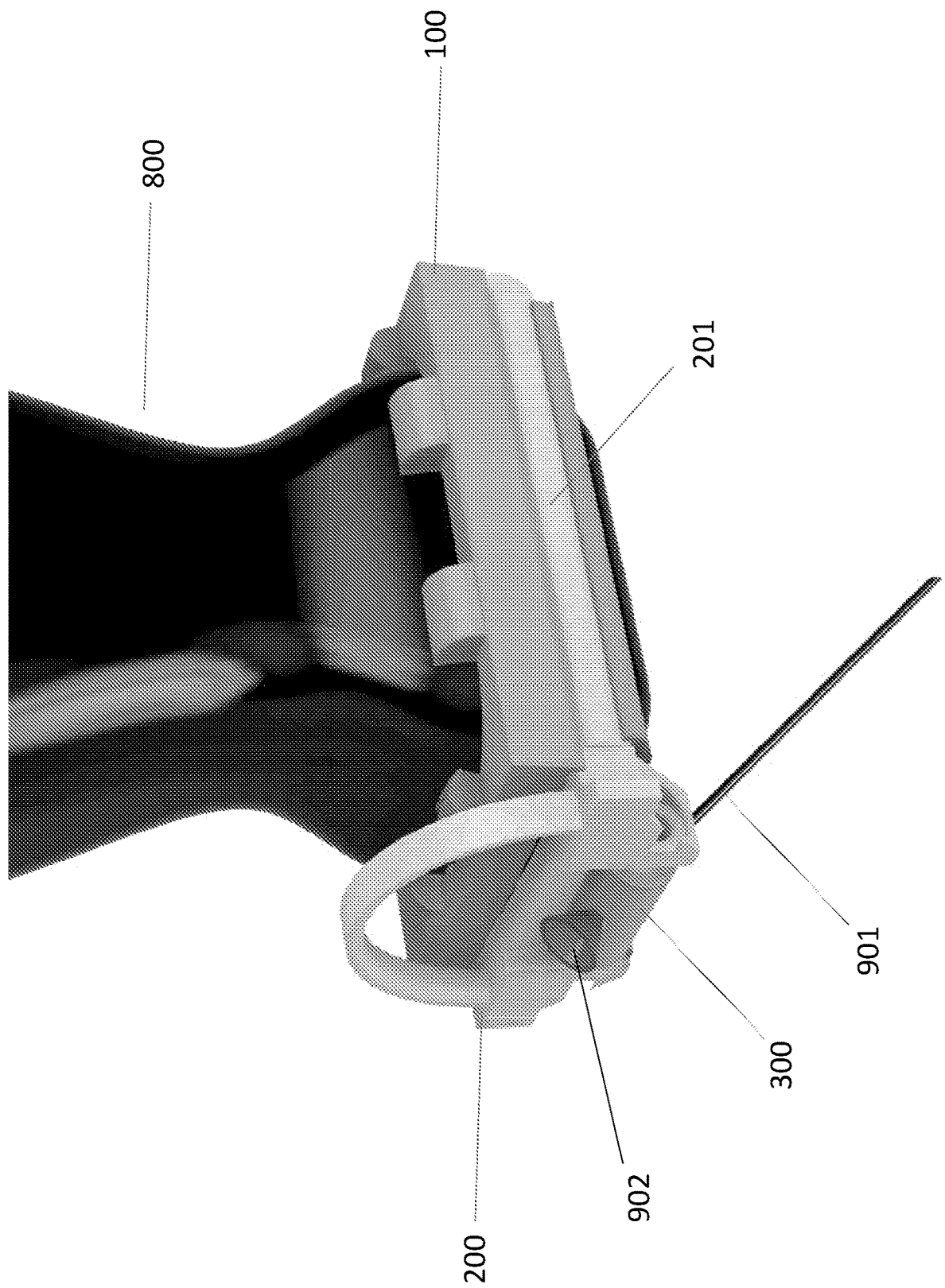
FIG. 9 demonstrates one embodiment of an ultrasound imaging device inserted into the body of a vascular access device and in which a needle is inserted into a needle guide that is configured into a rail guide secured around the body of a vascular access device in the longitudinal ultrasound imaging plane.
Figure 10:
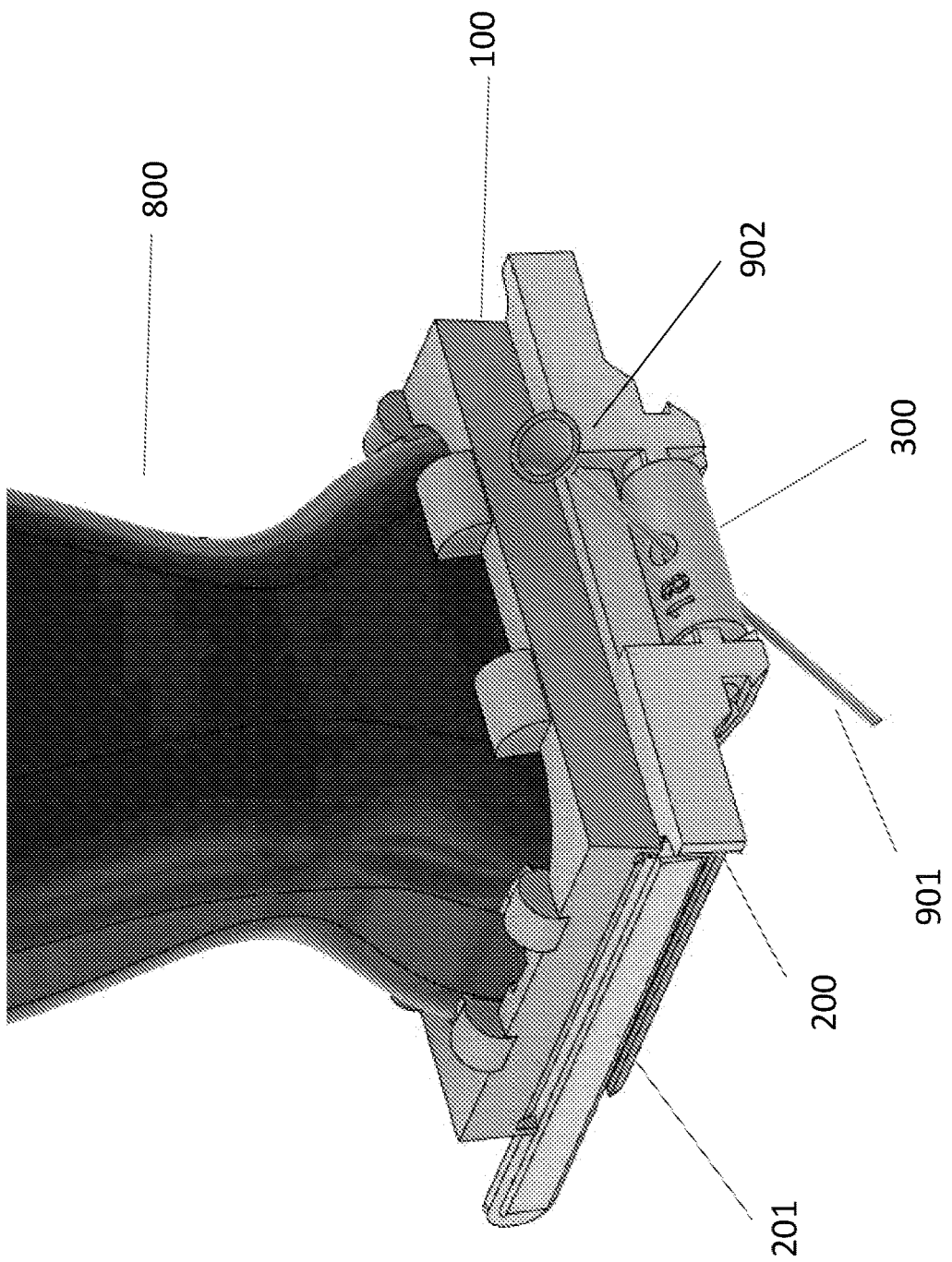
FIG. 10 shows one example of an ultrasound imaging device inserted into the body of an embodiment of a vascular access device configured for imaging in the transverse ultrasound imaging plane.

In specific embodiments, the rail guide arms 201 can be comprised of either pre-indented holes and/or nodules and/or magnets. As shown in FIG. 6, there may be an array of magnets embedded within the rail guide arms 201 that would align with complimentary magnets that are localized and fitted into the rail guide tracks 103 (also shown in 501) on the main body 100.

Outside of the rail guide tracks 103 there can be markers and positioning system guides to allow the user to set and adjust the rail guide to particular lengths across the length scale, such as 1 mm-50 mm, for example. In particular embodiments, the range of the length scale is 1-50, 1-45, 1-40, 1-35, 1-30, 1-25, 1-20, 1-15, 1-20, 5-50, 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 30-50, 30-45, 30-40, 30-35, 35-50, 35-45, 35-40, 40-50, 40-45, or 45-50 mm, or any range derivable therein.

The adjustment point 202 can take a variety of shapes and configurations to allow for ease of pulling and pushing for adjustability of the rail guide arms 201 within the rail guide tracks 103. For example, adjustment point 202 may be fabricated with grip-enhancing patterning or thin film polymers under a variety of shapes such as flat, planar, circular, cylindrical, etc.

Rail guide 200 also comprises needle guide insertion points 203 that are configured to have inserted thereto a needle guide 300 The needle guide insertion points 203 are configured to allow for efficient insertion and release of the needle guide 300 into the rail guide 200. The needle guide insertion points 203 are configured to allow for a quick load-position-and-release, and this can take a variety of forms or a combination of magnetic; ferromagnetic, superparamagnetic, electro-magnetic; manufactured channel mechanisms to allow for facile loading of the needle guide 300 into the rail guide 200. In a specific embodiment, needle guide insertion points 203 each comprise a groove that is configured for the needle guide 300 to only go in one direction. In specific cases, the needle guide insertion points 203 each comprise a generally upside down letter "J" to which the needle guide is inserted and secured into. In some cases, each of the needle guide insertion points 203 on rail guide 200 comprise magnets and each of the corresponding ends 302 of the needle guide 300 also comprise magnets.

C. Needle Guide

Figure 3:
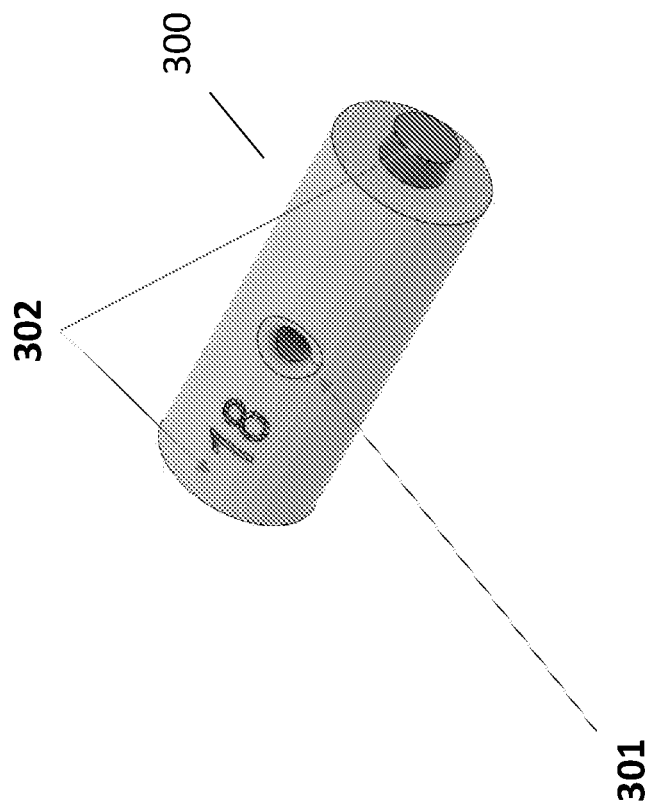
FIG. 3 provides one embodiment of a needle guide to be utilized in a rail guide with a body of a vascular access device.

FIG. 3 illustrates an embodiment of a needle guide 300. In specific embodiments, the needle guide 300 serves two primary functions. First, it stabilizes the needle through prefabricated needle channel 301. Secondly, the needle guide 300 has a load-position-and-release system (LPRS) that allows for both angular adjustment/positioning of the needle, as well as easy release of itself from the rail guide 200, as well as from the inserted needle, leaving behind the inserted needle.

The needle guide 300 is of a shape that allows rotation to provide movement of a needle when inserted into a needle channel 301 of the needle guide 300. At least part of the interior of the needle guide 300 is hollow so that a needle may traverse the entirety of the needle guide 300 when inserted into the needle channel 301. Thus, the needle channel 301 must be open from one side of the needle guide 300 to the other side of the needle guide 300. In specific embodiments, the needle guide 300 is generally cylindrical, rectangular, triangular, ridged, or polygonal in shape.

Figure 4:
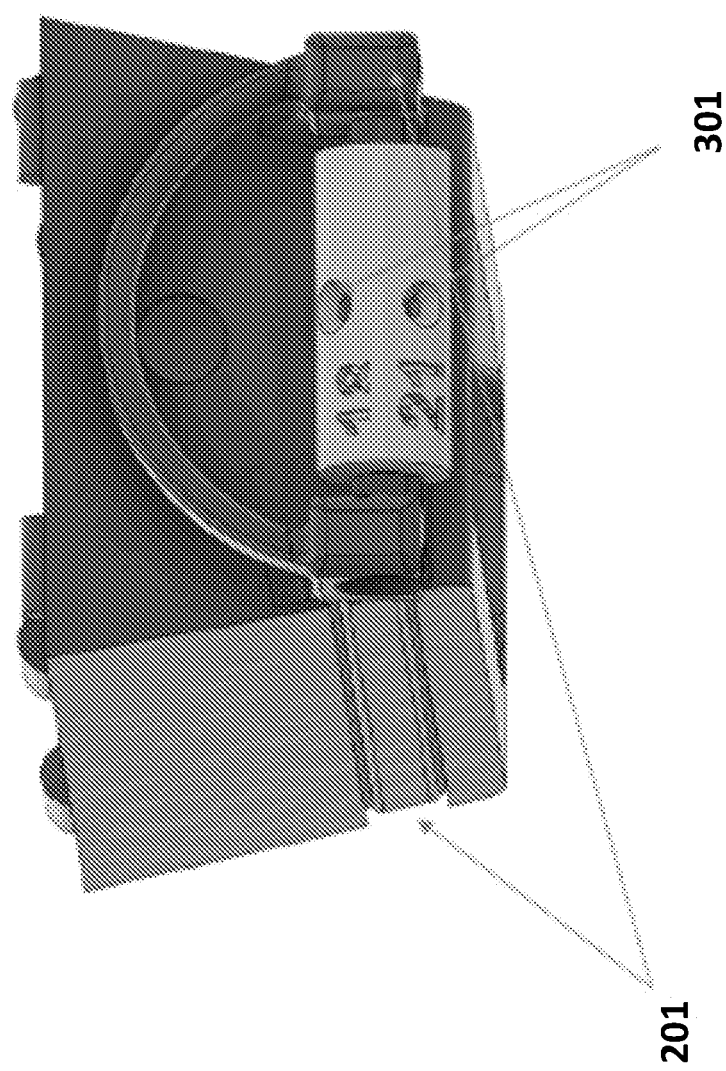
FIG. 4.0 shows a needle guide inserted into a rail guide that is secured around a body of a vascular access device.
Figure 11:
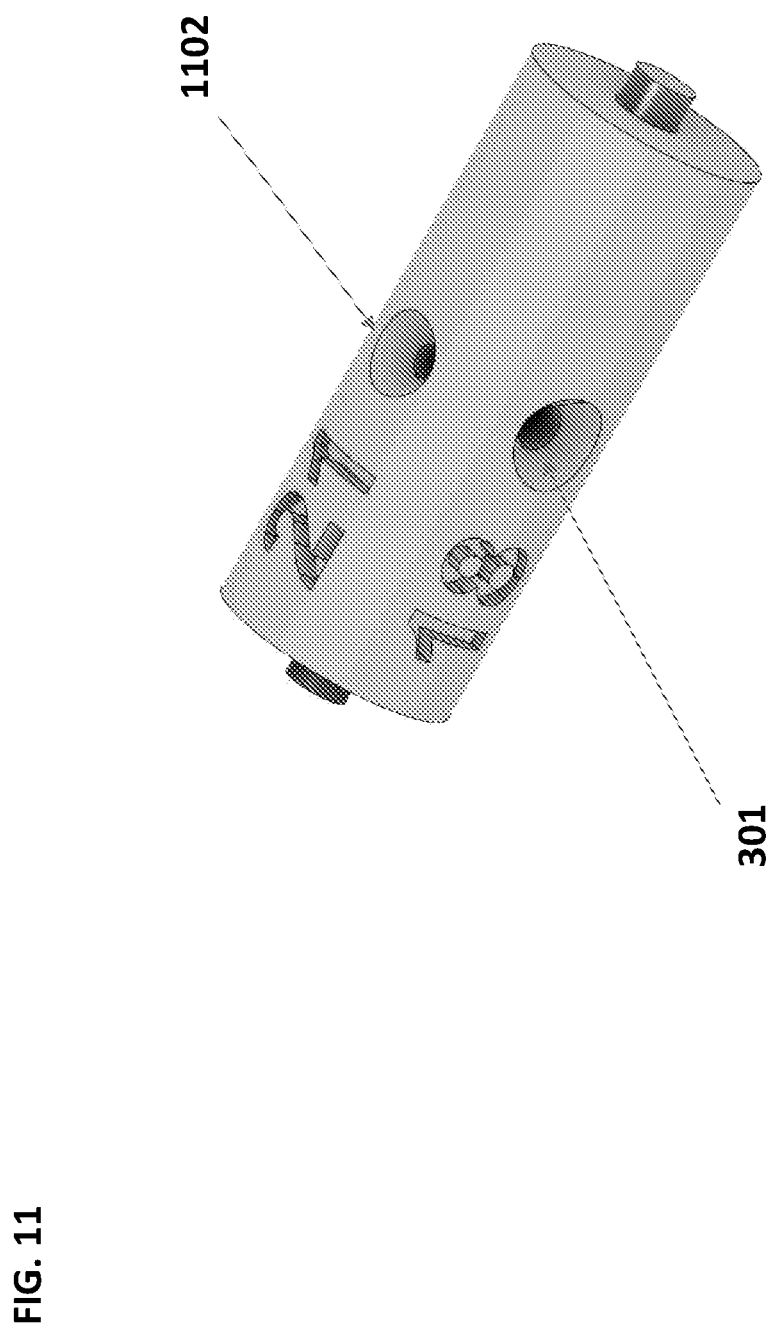
FIG. 11 demonstrates one embodiment of the needle access guide configured to accept either a 18 gauge or 12 gauge needle, as examples.

The needle guide 300 can be used with a variety of needle sizes (gauges) and provides both stability and free movement of the needle into the desired location. In some embodiments, in a needle guide 300 having only one needle channel 301, the needle guide 300 is selected based on the desired size of the needle channel 301 determined by a desired gauge of a needle. In other embodiments, a needle guide 300 has multiple needle channels 301 and in specific cases the multiple needle channels 301 are of different sizes to allow a variety of gauges of needles to be utilized (see FIGS. 4 and 11). A needle guide 300 may be fashioned such that different gauge needles can be placed through the same needle guide 300 without having to change out different needle guide 300 for different needles. FIGS. 4 and 11 show one example of how a 18 gauge and 21 gauge needle can be placed using a single needle guide 300. In specific cases, the different needle channels 301 (for example, for an 18 gauge needle) and 1102 (for example, for a 21 gauge needle) on a single needle guide 300 may or may not be offset from one another with respect to a circumferential line around the needle guide 300.

The needle guide 300 is configured to be able to insert into rail guide 200 at needle guide insertion points 203 of the rail guide 200. In doing so, needle guide ends 302 are configured to insert into the needle guide insertion points 203 such that the needle guide is secure in the rail guide 200 but also such that the needle guide ends 302 are able to rotate within the needle guide insertion points 203 to allow choices in position of the angle of the needle. The positioning of needle guide ends 302 within needle guide insertion points 203 is configured to allow for ease of loading of the needle guide 300 into rail guide 200 and also for removal of needle guide 300 from rail guide 200. The quick load-position-and-release section utilizing needle guide insertion points 203 (FIGS. 2 and 3) can take a variety of forms or a combination of magnetic; electro-magnetic; ferromagnetic; superparamagnetic and/or manufactured channel mechanisms to allow for facile loading of the needle guide 300 into the rail guide 200.

In any case, a needle guide 300 may be color-coded to match needle gauge universal coding specifications. The needle guide in addition or alternatively may have numbers, including patterned numbers, on the exterior to allow the user to select the correct needle size for that particular needle guide. The needle guide 300 may comprise markings and/or symbols and/or numerical characters that align with a complementary marking system on the rail guide 200 so that the correct angle of needle positioning can be selected.

In specific cases in which the needle will be inserted into a tubing of some kind, the diameter of the tubing (such as a central needle access line) in which the needle will be inserted determines what size needle may be accommodated.

The interior of the needle channel 301 may be coated with a variety of materials to modulate the desired friction and elasticity coefficient for needle movement dynamics.

The needle guide insertion points 203 into which the needle guide 300 inserts into the rail guide 200 may utilize a load-position-and-release system (LPRS), in specific embodiments. The LPRS serves one or two primary functions, in at least some cases. The first function is to allow easy detachment of the needle guide 300 from the rail guide 200 and the needle guide insertion points 203. The second function is to allow subsequent removal of the needle guide 300 from the needle 901 that has been inserted through the needle channel 301. In specific embodiments, in such cases the needle guide 300 may be comprised of at least two separate parts that are interlocked together such that complete removal of the needle guide 300 from the needle or an inserted device delivered through the needle guide may be made possible by unlocking the two or more separate components from one another. This interlocking mechanism may be based on a variety of mechanisms and/or materials such as magnets, ferromagnetics, superparamagnetics; electromagnetics; twist-locks; click locks; push locks, etc.

II. Methods of Using the Tissue Access Device

Embodiments of the disclosure allow for improvements of current methods for accessing tissues and/or organs, including blood vessels, in an individual in need thereof. The device allows for precise and accurate placement of a needle into a blood vessel and is designed to allow for smooth adjustment and operation that prevents imaging artifacts and hindered process flow.

In addition to catheter-based interventions, central venous and arterial access allows for rapid administration of fluids and medications in potentially life-saving applications. It is also used in emergency situations and is a procedure that is commonly performed in a medical facility, such as in an emergency room or intensive care unit of a hospital. Use of the device encompassed herein provides for safe central venous access, such as via the internal jugular vein, subclavian vein, femoral artery, or radial access in catheter-based interventions, for example. Additionally, in trauma settings, balloon tamponade via expeditious femoral access may be critical [18]. Therefore, the present disclosure provides means for successful access of a vessel that may be a life-altering procedural step.

During access of a vessel, there are a variety of procedures that can either utilize the venous or arterial pathways for entry into the body depending on the goal of the intervention. With respect to the ultrasound guided access of deeper arterial or venous structures, two different methodologies are typically employed: transverse and longitudinal. Transverse view of the vessels is advantageous in that the vascular structures are often seen more easily and in relation to other physical landmarks. However, visualizing the needle tip is more difficult as it is only a circular cross section on the ultrasound screen that may lead to difficulty identifying when the vessel is truly cannulated or conversely identifying inadvertent damage to the vessel wall. Alternatively, longitudinal access is more difficult to adopt early on in the process, as the vessel must be "opened" on the ultrasound screen so that it is divided length-wise. However, once this technique is mastered, the needle can then be clearly seen in its entirety while being inserted into the tissue. This imparts a complete visualization of the needle tip and prevents inadvertent trauma to the posterior wall of the artery or vein and to surrounding structures.

The tissue and/or organ access device of the disclosure is designed to decrease or remove the specialized skill required to keep the needle within the plane of the imaging cross section during either longitudinal or transverse access. This will not only minimize the chance of inadvertent trauma but will allow the operator to quickly access the vessel while visualizing the entire needle (and needle tip). Once the vessel is accessed and a wire is placed into the lumen of the vessel, the needle holder component of the device can be removed from the ultrasound unit through a novel technology using magnets (as one example) to keep the holder in place. This allows for the needle and holder (needle guide) to be removed safely over the wire that allows the procedure to proceed uninhibited without a change in current operator workflow.

The present disclosure utilizes a system for adjustability of the needle based on its configuration within a needle guide 300 that is positioned within a rail guide 200 having rail guide arms 201. The mobility of the needle in a longitudinal plane with respect to a surface is provided by the needle 901 being held in the rail guide 300 that moves with the rail guide 200 when it moves. This allows for accommodation of different tissue depth in accessing vessels (accounting for obesity, variation in anatomic positioning of arteries/veins, etc.)

The needle guide 300 has the ability to rotate around an axis. In specific embodiments, the needle guide 300 has full 360-degree adjustability of the needle guide around an axis. This allows for complete user control when attempting cannulation. Allows for more superficial cannulation if needed or otherwise avoiding areas of plaque, etc. Thus, given that the needle guide 300 can rotate about an axis, the angle by which a needle approaches an insertion point on an individual may be changed prior to entry. This gives the user a greater number of choices for angles of insertion into an individual. The angle may be changed by any of a variety of degrees, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, or more degrees. A range of angle in which the angle may be changed includes from 0-90, 0-85, 0-80, 0-75, 0-70, 0-65, 0-60, 0-55, 0-50, 0-45, 0-40, 0-35, 0-30, 0-25, 0-20, 0-15, 0-10, 0-5, 1-90, 1-85, 1-80, 1-75, 1-70, 1-65, 1-60, 1-55, 1-50, 1-45, 1-40, 1-35, 1-30, 1-25, 1-20, 1-15, 1-10, 1-5, 5-90, 5-85, 5-80, 5-75, 5-70, 5-65, 5-60, 5-55, 5-50, 5-45, 5-40, 5-35, 5-30, 5-25, 5-20, 5-15, 5-10, 10-90, 10-85, 10-80, 10-75, 10-70, 10-65, 10-60, 10-55, 10-50, 10-45, 10-40, 10-35, 10-30, 10-25, 10-20, 20-90, 20-85, 20-80, 20-75, 20-70, 20-65, 20-60, 20-55, 20-50, 20-45, 20-40, 20-35, 20-30, 20-25, 30-90, 30-85, 30-80, 30-70, 30-65, 30-60, 30-55, 30-50, 30-45, 30-40, 30-35, 35-90, 35-85, 35-80, 35-75, 35-70, 35-65, 35-60, 35-55, 35-50, 35-45, 35-40, 40-90, 40-85, 40-80, 40-75, 40-70, 40-65, 40-60, 40-55, 40-50, 40-45, 50-90, 50-85, 50-80, 50-75, 50-70, 50-65, 50-60, 50-55, 60-90, 60-80, 60-75, 60-70, 60-65, 70-90-70-85, 70-80, 70-75, 75-90, 75-85, 75-80, 80-90, 80-85, or 85-90 degrees, for example. When the angle by which a needle approaches an insertion point needs to be changed prior to entry, the angle may be decreased or increased.

In particular embodiments, the needle guide 300 is detachable with respect to the rail guide 200. In specific cases, the needle guide detaches through a novel sliding mechanism that allows for safe placement of a wire and exchange of the needle for a sheath to start any endovascular procedure (central or peripheral). In certain embodiments, a mechanism that allows for removal of the needle guide 300 from the rail guide 200 may be of any physical configuration. The mechanism may be a load-position-and-release system. In specific embodiments, the mechanism is magnetic, physically interlocking, a channel system, a combination thereof, and so forth. The mechanism may be manual or it may be automatic. The need to remove the needle guide 300 from the rail guide 200 may be made by the user dependent upon the medical procedure, including feedback from the imaging device. In some embodiments, the needle guide is used as two or more separate parts that are interlocked together such that complete removal of the needle guide 300 from the needle or an inserted device occurs by unlocking the two or more separate components from one another, such as using magnets, ferromagnetics, superparamagnetics; electromagnetics; twist-locks; click locks; push locks, etc.

The use of the vascular access device may be in conjunction with any ultrasound transducer head or any imaging device, such as CT, PET, optical/infrared imaging devices, for example, whereby the active imaging element can fit into the main body of the device. The device may be configured to allow for both transverse and/or longitudinal ultrasound-guided needle access using either separate devices that are specifically dedicated for either longitudinal or transverse imaging, or using a single device by incorporating both longitudinal and transverse rail guides and relative components thereof. In specific embodiments, the device can be fully robotized whereby the robotic function incorporates either manual or autonomous (ultrasound feedback) control of needle placement.

The placement of the needle in some cases may be derived based on utilization of markers on the corresponding rail guide 200 and needle guide 300. This allows for specific depths and angles of insertion to be achieved. In specific cases, this may be utilized in conjunction with a 'look up table' methodology where a predetermined depth is precalculated and the correct marking system shown.

In particular embodiments, a vascular access device of the disclosure is utilized with an ultrasound device so that a needle may be efficiently and accurately placed for access to a blood vessel of any kind. Prior to use, a gauge of a needle is determined that then allows for selection of a needle guide 300 having a suitable sized opening of a needle channel 301 through which the needle will traverse. The selected needle guide 300 is inserted into the rail guide 200 at the needle guide insertion points 203. In at least some cases, the needle 901 on the end opposite the pointed end comprises an entry point 902 (FIG. 9) through which a wire or other narrow long entity may be threaded into the needle 901. The rail guide 200 is positioned in the body 100 through the rail guide arms 201 being inserted in the rail guide tracks 103 of the body 100. The rail guide 200 may be inserted in the body 100 either before or after the ultrasound imaging device 800 is placed in the body 100. Once the needle guide 300 is placed in the rail guide 200, the rail guide 200 is placed in the body 100, and ultrasound imaging device 800 is placed in the body 100 (and this may occur in any order, in some cases), the vascular access device may be used.

Placement of the needle 901 at the desired site on the body of an individual in need of vascular access is adjustable because of the unique configuration of the device. When the image provides feedback that positioning of a needle needs to be changed, the device is adjusted. In specific embodiments, when a needle needs to be moved longitudinally with respect to the body of the individual, the rail guide 200 having the needle guide 300 with a needle 901 inserted therein is moved longitudinally by moving the rail guide 200 along the rail guide tracks 103. In specific embodiments, the rail guide 200 is moved by the user holding onto the adjustment point 202. One or more adjustments longitudinally may be required, including based on information from the imaging device.

In some cases, an ultrasound device provides feedback that informs the user that the angle by which the needle 901 is approaching the body needs to be adjusted. In such cases, the needle guide 300 may be rotated about a rotational axis to change the angle by which the needle is positioned. As a result, the needle may be inserted into the body at an appropriate angle. One or more adjustments rotationally of the needle guide 300 may be required, including based on information from the ultrasound device.

In certain embodiments, the longitudinal adjustment of the rail guide 200 to allow suitable placement of the needle 901 on a desired location of the body and the rotational adjustment of the needle guide 300 around a rotational axis to allow for suitable angle of insertion of a needle into the body are both needed, whereas in other cases only one of the two movements is required.

Once the needle 901 is suitable placed into the body of the recipient individual and the device is no longer needed (for example, because the ultrasound information may no longer be needed), the rail guide 200 with the needle guide 300, or the needle guide 300 alone, with or without the needle 901 therein, may be detached from the system. In some cases, the device including the needle guide 300 is removed, leaving an inserted medical tool, such as a catheter or wire.

In particular embodiments, methods and systems of the disclosure are utilized for a tumor biopsy. An individual suspected of having a tumor or known to have a tumor may be subjected to methods and systems of the disclosure for guided access to the tumor using an imaging device and the needle positioning device for accurate positioning for the tumor.

In some embodiments, methods and systems of the disclosure are utilized for drug delivery, wherein the needle positioning device is utilized with an imaging device, and the needle positioning device places a medical device that allows for delivery of the drug, for example through a tubing.

REFERENCES

All publications mentioned in this specification are indicative of the level of those skilled in the art to which the invention pertains. All publications herein are incorporated by reference to the same extent as if each individual publication was specifically and individually indicated to be incorporated by reference in their entirety.

1. J Evans: Global Market for Catheters. BCC Research: 51-52 2019
2. J J Siracuse, M T Menard, M H Eslami, et al.: Vascular Quality Initiative. Comparison of open and endovascular treatment of patients with critical limb ischemia in the Vascular Quality Initiative. J Vasc Surg. 63 (4):958-965.e1 2016
3. J Kalish, M Eslami, D Gillespie, et al.: Routine use of ultrasound guidance in femoral arterial access for peripheral vascular intervention decreases groin hematoma rates. J Vasc Surg. 61 (5):1231-1238 2015
4. H M Farouque, J A Tremmel, F Raissi Shabari, et al.: Risk factors for the development of retroperitoneal hematoma after percutaneous coronary intervention in the era of glycoprotein IIb/IIIa inhibitors and vascular closure devices. J Am Coll Cardiol. 45 (3):363 2005
5. R C Lo, M T Fokkema, T Curran, et al.: Routine use of ultrasound-guided access reduces access site-related complications after lower extremity percutaneous revascularization. J Vasc Surg. 61 (2):405-412 2015
6. F Erol, Ş Arslan, İÔ Yûksel, et al.: Determinants of iatrogenic femoral pseudoaneurysm after cardiac catheterization or percutaneous coronary intervention via the femoral artery. Turk Kardiyol Dern Ars. 43 (6):513-519 2015.
7. B D Coley, A C Roberts, B D Fellmeth, et al.: Postangiographic femoral artery pseudoaneurysms: further experience with US-guided compression repair. Radiology. 194:307-311 1995
8. L Eisenberg, E K Paulson, M A Kliewer, et al.: Sonographically guided compression repair of pseudoaneurysms: further experience from a single institution. AJR Am J Roentgenol. 173:1567-1573 1999
9. P V Tisi, M J Callam: Treatment for femoral pseudoaneurysms. Cochrane Database Syst Rev. (11)2013 CD004981
10. R C Lo, M T Fokkema, T Curran, et al.: Routine use of ultrasound-guided access reduces access site-related complications after lower extremity percutaneous revascularization. J Vasc Surg. 61 (2):405-412 2015
11. M Kelm, S M Perings, T Jax, et al.: Incidence and clinical outcome of iatrogenic femoral arteriovenous fistulas: implications for risk stratification and treatment. J Am Coll Cardiol. 40:291-297 2002
12. M A Ohlow, M A Secknus, H von Korn, et al.: Incidence and outcome of femoral vascular complications among 18,165 patients undergoing cardiac catheterisation. Int J Cardiol. 135 (1):66-71 2009
13. C Thalhammer, A S Kirchherr, F Uhlich, et al.: Post-catheterization pseudoaneurysms and arteriovenous fistulas: repair with percutaneous implantation of endovascular covered stents. Radiology. 214:127-131 2000
14. J Waigand, F Uhlich, C M Gross, et al.: Percutaneous treatment of pseudoaneurysms and arteriovenous fistulas after invasive vascular procedures. Catheter Cardiovasc Interv. 47:157-164 1999 10376495
15. B Onal, S Kosar, T Gumus, et al.: Postcatheterization femoral arteriovenous fistulas: endovascular treatment with stent-grafts. Cardiovasc Intervent Radiol. 27:453-458 2004
16. FIG. 2f from: Irimia R, Gottschling M (2016) Taxonomic Revision of Rochefortia Sw. (Ehretiaceae, Boraginales). Biodiversity Data Journal 4: e7720
17. "Vascular Access Procedures" https://www.radiologyinfo.org/en/info.cfm?pg=vasc_access
18. BCC Staff: Intravenous Therapy and Vein Access Global Markets. BCC Research: 2019.
19. Vascular Access Device Market." Markets and Markets. Jul. 2017. https://www.marketsandmarkets.com/PressReleases/vascular-access-device.asp
20. Slicker, K., Lane, W. G., Oyetayo, O. O., Copeland, L. A., Stock, E. M., Michel, J. B., & Erwin, J. P. (2016). Daily cardiac catheterization procedural volume and complications at an academic medical center. Cardiovascular diagnosis and therapy, 6(5), 446.
21. "Cook Micropuncture Introducer Set." eSutures.com. https://www.esutures.com/product/O-in-date/54-cook/794-introducers/

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A system for facilitating access to tissue and/or organ using an imaging device, comprising:
    (a) a body component having four sides, wherein said body component is configured to have the imaging device insertable therein, wherein the body component has an opening to transmit an image;
    (b) a needle guide comprising a longitudinal axis along its length and comprising a width, wherein the needle guide is rotationally moveable along the longitudinal axis and wherein there is at least one opening that traverses the width of the needle guide, wherein the opening is suitably sized for positioning a needle;
    (c) a needle guide positioning apparatus comprising one or more arms and comprising means for inserting the needle guide therein, wherein at least two of the sides of the body component comprise tracks through which the arms of the needle guide positioning apparatus are insertable therein,
    wherein each body component track comprises one or more magnets and wherein interior sides of each arm comprise one or more complementary magnets that align with the one or more magnets in the tracks; and
    wherein the needle guide is detachable from the needle guide positioning apparatus.

2. The system of claim 1, further defined as a system for facilitating access to a vessel.

3. The system of claim 1, wherein the body component comprises one or more mounting components configured to hold the imaging device in the body component.

4. The system of claim 1, wherein the needle guide comprises 2, 3, 4, 5, 6, or more openings that traverse the width of the needle guide.

5. The system of claim 4, wherein multiple of the openings comprise different sizes to accept needles of different gauges.

6. The system of claim 1, wherein the arms of the needle guide positioning apparatus each comprise an interior side and an exterior side, wherein when the needle guide positioning apparatus is not in the tracks of the body component, the interior sides of the arms face one another.

7. The system of claim 1, wherein the body component is configured as a parallelogram and wherein a first parallel pair of two sides is the same length as a second parallel pair of two sides.

8. The system of claim 1, wherein the body component is configured as a parallelogram and wherein a first parallel pair of two sides is a longer length than a second parallel pair of two sides.

9. The system of claim 7, wherein one or both of the first parallel pair of two sides and second parallel pair of two sides have the tracks through which the arms of the needle guide positioning apparatus are insertable therein.

10. The system of claim 1, wherein the needle guide positioning apparatus comprises a means for inserting the needle guide therein that is magnetic, ferromagnetic, superparamagnetic, electro- magnetic, is a manufactured channel, or a combination thereof.

11. The system of claim 1, wherein the needle guide positioning apparatus comprises a handle.

12. The system of claim 1, wherein the needle guide comprises two or more components that are configured to be interlockable and detachable from one another.

13. The system of claim 1, wherein the imaging device is an ultrasound device.

14. A method of accessing a region of a tissue and/or organ of an individual by needle and with an imaging device, comprising the step of moveably positioning the needle at the body of the individual using the system of claim 1.

15. The method of claim 14, further defined as using a signal from the imaging device to provide information about the tissue and/or organ of the individual, wherein the information informs a user of the system about a desired location and/or angle for the needle.

16. The method of claim 14, further defined as positioning the system at the body of the individual and slidably moving the needle guide positioning apparatus to allow for a desired position of the needle at the body of the individual.

17. The method of claim 15, further defined as rotating the needle guide along the longitudinal axis to position the needle at a desired angle with respect to the body of the individual.

18. The method of claim 16, wherein following positioning of the needle at the body of the individual, the needle guide is detached from the system.

19. The method of claim 17, wherein following positioning of the needle at the body of the individual, the needle guide is detached from the system and the needle guide is detached from the needle.

20. The method of claim 14, further defined as using two separate imaging devices, wherein a first imaging device is used for transverse imaging-guided needle access, and a second imaging device is used for longitudinal imaging-guided needle access.

21. The method of claim 14, wherein the imaging device is configured for transverse and/or longitudinal imaging-guided needle access, said device comprising both longitudinal and transverse rail guides.

* * * * *